United States Patent [19]
Byram et al.

[11] Patent Number: 4,834,083
[45] Date of Patent: May 30, 1989

[54] AEROSOL DEVICE

[75] Inventors: David C. Byram; Gerald W. Teiken; Ralph D. Whaley, all of St. Paul, Minn.

[73] Assignee: Minnesota Mining and Manufacturing Company, St. Paul, Minn.

[21] Appl. No.: 193,420

[22] Filed: May 12, 1988

[51] Int. Cl.$^4$ .................. A61M 11/00; A61M 11/04
[52] U.S. Cl. .......................... 128/200.23; 128/200.14; 222/162; 222/402.11; 222/402.12; 222/402.13
[58] Field of Search ................ 128/200.14, 200.23; 222/162, 402.11, 402.12, 402.13

[56] References Cited

U.S. PATENT DOCUMENTS

| | | |
|---|---|---|
| 3,001,524 | 9/1961 | Maison et al. . |
| 3,191,867 | 6/1965 | Helms .............................. 128/200.23 |
| 3,506,004 | 4/1970 | Mann et al. ..................... 222/402.13 |
| 3,636,949 | 1/1972 | Kropp ............................. 128/200.23 |
| 3,732,864 | 5/1973 | Thompson et al. . |
| 3,789,843 | 2/1974 | Armstrong et al. ............ 128/200.23 |
| 4,292,966 | 10/1981 | Mono et al. . |
| 4,637,528 | 1/1987 | Washimski et al. . |
| 4,664,107 | 5/1987 | Wass et al. . |
| 4,678,106 | 7/1987 | Newell et al. . |
| 4,765,515 | 8/1988 | Lippman ............................ 222/162 |
| 4,771,769 | 9/1988 | Hegemann et al. ................. 222/162 |

OTHER PUBLICATIONS

Physicians' Desk Reference 1988, 42, pp. 1872-1873.

Primary Examiner—Edgar S. Burr
Assistant Examiner—Kimberly L. Asher
Attorney, Agent, or Firm—Donald M. Sell; Walter N. Kirn; Robert W. Sprague

[57] ABSTRACT

The invention is a dispenser for use with aerosol formulations for inhalation therapy. The dispenser is small, conveniently carried, and features means to prevent unintended actuation of the aerosol canister and means to prevent dust and dirt from entering the dispenser during storage.

18 Claims, 3 Drawing Sheets

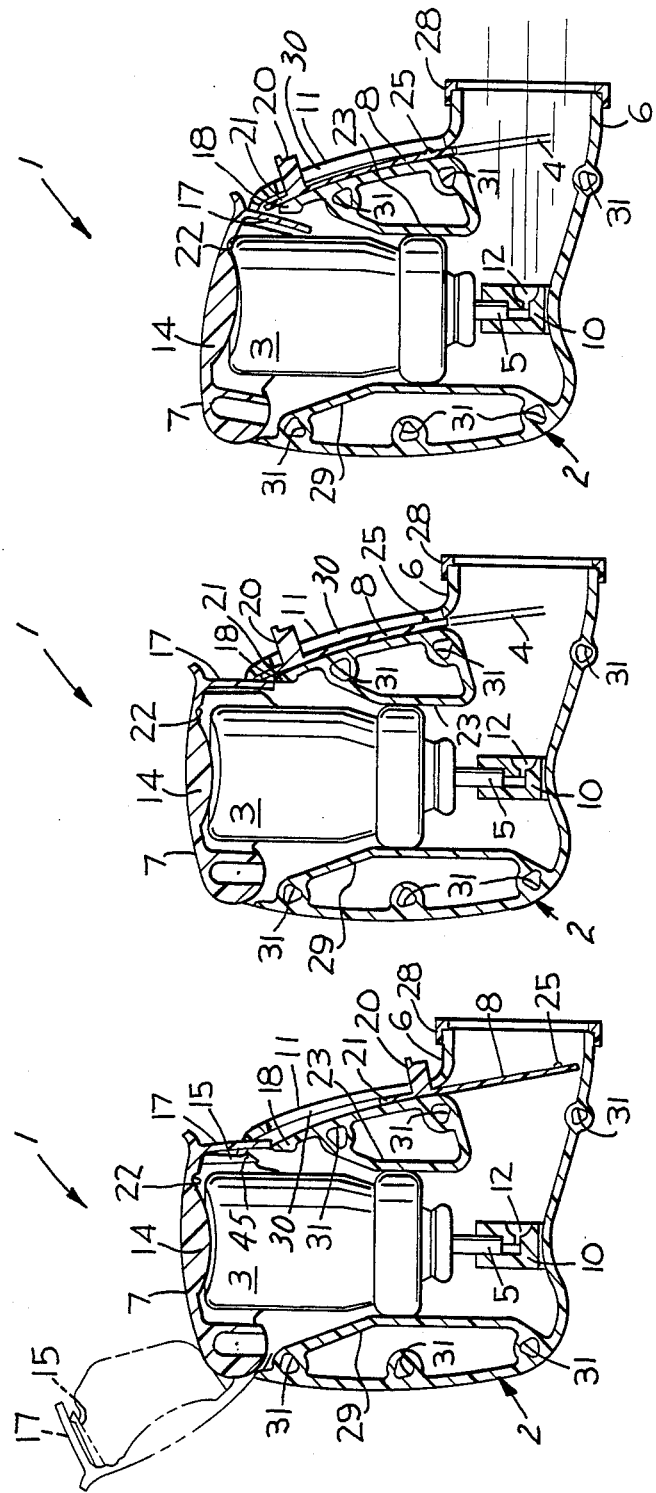

AEROSOL DEVICE

TECHNICAL FIELD

This invention relates to dispensers for use with aerosol container assemblies which contain medicaments for inhalation therapy.

BACKGROUND OF THE INVENTION

Dispensers for aerosol formulations are in common use. In their simplest form, these dispensers comprise an L-shaped plastic device adapted at one end to receive an aerosol canister and terminating at the other end in a mouthpiece. These devices require that the user actuate the aerosol canister by manually depressing the canister, without any mechanical advantage, to the point of actuation. These simple dispensers such as that the disclosed in U.S. Pat. No. 3,001,524 provide no means to prevent accidental actuation, nor do they provide a means beyond friction fit of assuring that the aerosol canister remains in place during storage.

Dispensers with apparatus for closing the mouthpiece are known. There is disclosed in U.S. Pat. No. 4,637,528 a retractable, pivotable dispenser for aerosol formulations. The dispenser includes a removable cap for the mouthpiece which serves to protect the dispenser from dirt and dust when stored in the retracted position. Similarly, U.S. Pat. No. 4,292,966 discloses a retractable dispenser which in its retracted state has a flexible tongue covering the opening in the mouthpiece. In the elongated position the tongue is removed from the mouthpiece. These dispensers, however, provide no means to prevent unintended actuation of the aerosol canister if they are stored with the canister in place.

There exist aerosol dispensers which employ latch mechanisms to prevent accidental actuation. Disclosed in U.S. Pat. No. 4,664,107 is an inhalation-actuable dispenser wherein a latch mechanism prevents the actuation by inhalation absent the application of force by the user to the aerosol container. Untimely actuation and administration of an improper dose of medicament is thus prevented. Similarly, U.S. Pat. No. 3,732,884 discloses an inhalation-actuable dispenser comprising a gate which blocks actuation of the aerosol unless the user is inhaling through the device or unless the device is not in an upright position.

Unintended actuation has been prevented by other means as well. There is available from Sandoz an L-shaped dispenser wherein the aerosol container is stored in the mouthpiece and a dust cap covers the opposite end of the dispenser. Thus, the dispenser is protected from dust and dirt during storage, and unintended actuation is prevented. However, considerable assembly is required to take the dispenser from storage to use. This device is described on pages 1872-1873 of the Physicians' Desk Reference, 42nd Edition, 1988.

Last, U.S. Pat. No. 4,678,106 discloses a dispenser with a housing, a cover for the mouthpiece, and an actuator all pivotally connected to one another. When the cover is closed, the actuator can not be made to contact the canister, and actuation is prevented. When the cover is pivoted to the open position, the actuator is made to contact the canister and the canister may be actuated.

SUMMARY OF THE INVENTION

The present invention is a dispenser for use with an aerosol container, the aerosol container having a valve for dispensing aerosol, the valve having a hollow valve stem which is movable relative to the container between an extended closed position and a depressed open position for discharge of aerosol, the dispenser comprising:

a housing with a front face terminating in a mouthpiece, which front face has an inside surface and which housing is adapted to receive an aerosol container and comprises a support block with a socket adapted to receive the valve stem, which support block has an orifice allowing open communication between the valve and the mouthpiece;

an actuator manually depressable between a closed position and an actuating position, having a first end pivotally mounted to the housing, a second manually depressable end, and a releasably engageable stop means to prevent unintended depression of the manually depressable end to the actuating position; and a catch means for preventing unintended depression of the actuator, which means is engageable with the stop means of the actuator when the actuator is in the closed position; and a gate means to open and close the mouthpiece, which gate means is mounted on the front face of the housing and comprises a wall section and a lift means to slide the wall section between a closed position in which the stop means of the actuator is engageable with the catch means, and the open communication between the valve and the mouthpiece is interrupted, and an open position in which open communication exists between the valve and the mouthpiece, and the stop means of the actuator is not engageable with the catch means thus permitting manual depression of the actuator to the actuating position.

The present invention provides a small, conveniently carrier dispenser for use with aerosol container assemblies which contain medicaments for inhalation therapy. While retaining the conventional drug delivery configuration of aerosol dispensers that have been in use for many years, the dispenser of the present invention employs novel features that enhance the convenience of carrying and using aerosol medicaments. The dispenser of the present invention features a manually depressable actuator equipped with a stop means which, through engagement with a catch means mounted on the housing, prevents unintended actuation of the aerosol container, in conjugation with a gate which is slideable between a closed position and an open position. In the closed position, the gate occludes the mouthpiece of the dispenser and the stop means and catch means are engageable such that unintended actuation of the aerosol container is prevented. In the open position, the gate has been removed from the mouthpiece and the stop means cannot engage the catch means. Thus, the aerosol container can be actuated only when the gate is in the open position, and unintended actuation of the dispenser is rendered unlikely.

In a preferred embodiment of the present invention, the actuator may be pivoted between an open position in which an aerosol container may be placed inside or removed from the dispenser, and a closed position in which the dispenser is suitable for storage. The actuator further includes a latch means which engages with a flange on the housing to prevent accidental opening of the actuator and subsequent displacement of the aerosol container.

In another preferred embodiment, the actuator includes a boss means which provides the user a mechanical advantage and facilitates the actuation of the aerosol container upon further depression of the closed actuator to an actuating position.

BRIEF DESCRIPTION OF THE DRAWINGS

The invention will be more thoroughly described with reference to the drawings, wherein like reference numerals refer to like parts in the several views.

FIG. 4 is a central cross sectional view of the embodiment of the dispenser shown in FIG. 1, wherein the dispenser is in the inactive mode, with the gate in the closed position. The housing is shown in section.

FIG. 5 is a central cross sectional view of the embodiment of the dispenser shown in FIG. 1, wherein the dispenser is in the ready mode, with the gate in the open position. The housing is shown in section.

FIG. 6 is a central cross sectional view of the embodiment of the dispenser shown in FIG. 1, wherein the dispenser is in the actuation mode, with the gate in the open position and the actuator depressed such that the aerosol is being discharged. The housing is shown in section.

DETAILED DESCRIPTION OF THE PREFERRED EMBODIMENT

Figure 1:
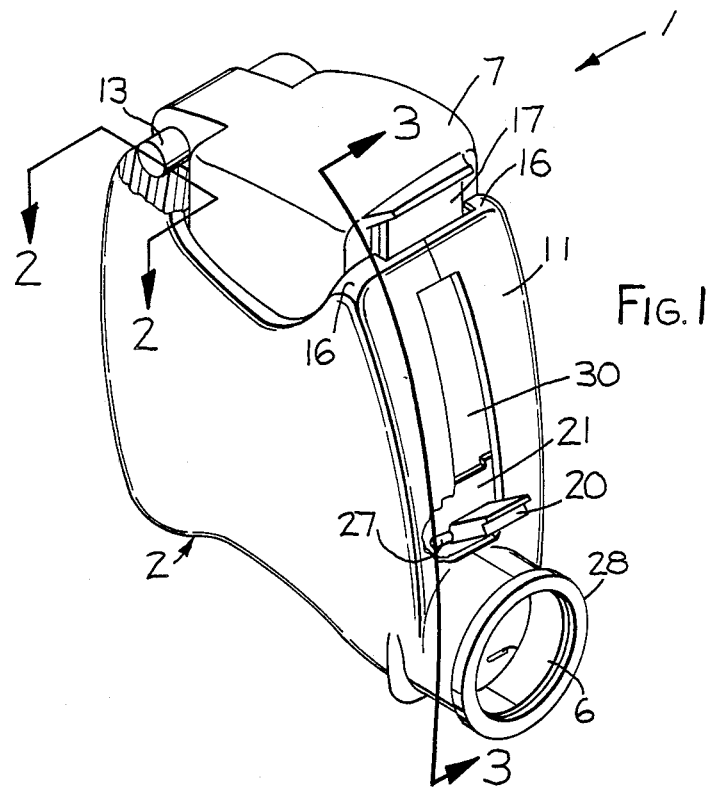
FIG. 1 is a perspective view of an embodiment of a dispenser according to the present invention.
Figure 2:
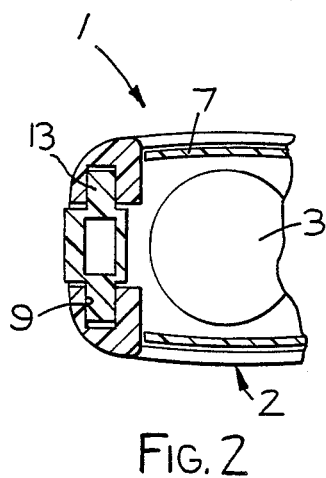
FIG. 2 is a partial cross sectional view of the embodiment of the dispenser shown in FIG. 1.

Referring to FIGS. 1-6 there is shown an embodiment of the dispenser of the present invention, generally designated by the reference numeral 1.

Housing 2 comprises a front aerosol container assembly support structure 23 and a rear aerosol container assembly support structure 29, which structures serve to define a chamber into which the aerosol container assembly 3 may be inserted stem down. Aerosol container assembly 3 contains, for example, a medicament and an aerosol propellant, and comprises a metering valve in a hollow valve stem 5 fixed in one end of the aerosol container assembly 3. The valve stem 5 is movable relative to the container 3 between an extended closed position and a compressed open position in which a metered dose of the aerosol is dispensed through the valve stem 5. Housing 2 further comprises a front section 11 which terminates in a mouthpiece 6 through which mouthpiece the user is to receive the metered dose of aerosol formulation.

Housing 2 additionally comprises a flange 16, a catch 18, and a nozzle block 10 having a socket adapted to receive the valve stem 5, which nozzle block has a through orifice 12 adapted to establish open communication between valve stem 5 and mouthpiece 6 and is further adapted to direct the aerosol discharge from the valve stem 5 through the mouthpiece 6. The housing 2 is adapted via an appropriately sized cylindrical bore 9 to accommodate the pivotally attached actuator 7.

Another feature of housing 2 is track 4 which serves to guide the travel of the gate 8 when gate 8 moves between its open position and its closed position.

As shown in FIG. 4, actuator 7 is movable between an open position and a closed position, in which open position an aerosol container assembly may be placed inside or removed from the dispenser 1. In the closed position, actuator 7 is manually depressable between the closed position (FIG. 5) and an actuating position (FIG. 6). Actuator 7 comprises a hinge pin 13 adapted to pivotally attach one end of the actuator 7 at cylindrical bore 9 of the housing 2. The portion 7a of the actuator between the hinge pins 13 comprises an open-ended chamber 7b. The actuator 7 is further adapted to make contact when in the closed position with the top of an inserted aerosol container assembly 3, preferably via a boss means 14. The purpose of the hinged actuator 7 and the boss 14 is to provide the user with a mechanical advantage and to thus facilitate actuation of aerosol container assembly 3 upon manual depression of actuator 7 from the closed position to the actuating position. Upon such manual depression of the actuator 7 the valve stem 5 will be depressed and a metered dose of the aerosol formulation will be dispensed through the orifice 12 toward the mouthpiece 6 for inhalation by the user. To prevent any escape of the aerosol formulation upwardly out of the nozzle block 10 and to accommodate variation in the size of valve stem 5, the socket in the nozzle block of the housing may be tapered to provide a friction fit between the value stem 5 and the socket.

Actuator 7 also includes a latch 15 adapted to releasably engage the flange 16 (best seen in FIG. 3) of the housing 2 when the actuator 7 is in the closed position. Thus, accidental opening of the dispenser 1 and subsequent displacement of the aerosol container assembly 3 is prevented. However, actuator 7 can be easily opened by the user if desired (for replacement of the aerosol container assembly 3, for example) by application of sufficient force to free latch 15 from engagement with flange 16.

A further constituent of the actuator 7 is stop 17, adapted to engage the catch 18 of housing 2 when the actuator 7 and the gate 8 are in their closed positions. With stop 17 and catch 18 thus engaged, manual depression of the actuator and subsequent discharge of the aerosol formulation are prevented.

Actuator 7 also features relief 22, which is in an arc of the same radius as the aerosol container assembly 3 and is adapted to prevent contact between the edge of the container 3 and actuator 7 when actuator 7 is manually depressed to the actuating position.

Gate 8 comprises a wall section, a lift means represented by tab 20, and a deflector means 21. Gate 8 is integral with the housing 2 such that gate 8 slides between the inside surface of the front section 11 of the housing 2 and the front aerosol container assembly support structure 23. As is best seen in FIG. 1, tab 20 is accessible through a slot 30 in front section 11 so as to facilitate sliding the gate between the open and closed positions. With gate 8 in the closed position (FIG. 4), the wall section occludes the mouthpiece 6 and thus interrupts open communication between the valve stem 5 and the mouthpiece 6. Gate 8 thus functions as a dust cover, preventing dust, dirt, lint and the like from entering housing 2 during storage. Furthermore, with gate 8 in the closed position the deflector means 21 is remote from stop 17. Hence, stop 17 remains engaged with catch 18, and manual depression of actuator 7 is prevented. With gate 8 in the open position (FIG. 5), the wall section is removed from the mouthpiece 6 and open communication between the valve stem 5 and the mouthpiece 6 is restored. On the other hand, with gate 8 in the open position, deflector section 21 displaces stop 17 from catch 18. Thus, manual depression of actuator 7 is allowed and discharge of a metered dose of aerosol formulation is possible.

Figure 3:
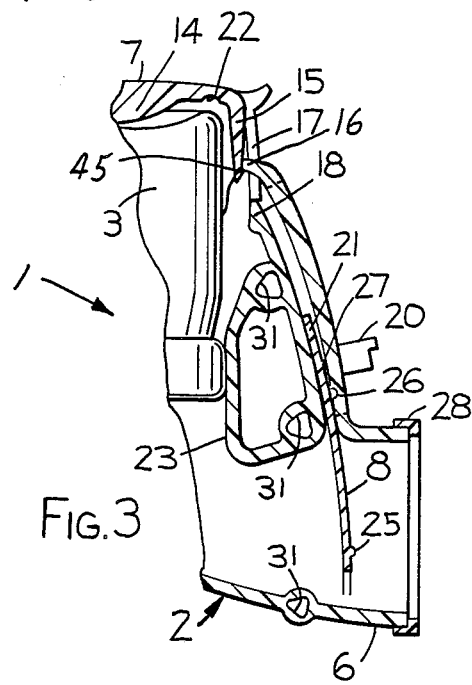
FIG. 3 is a partial cross sectional view of the embodiment of the dispenser shown in FIG. 1, wherein the gate is partially retracted.
Figure 7:
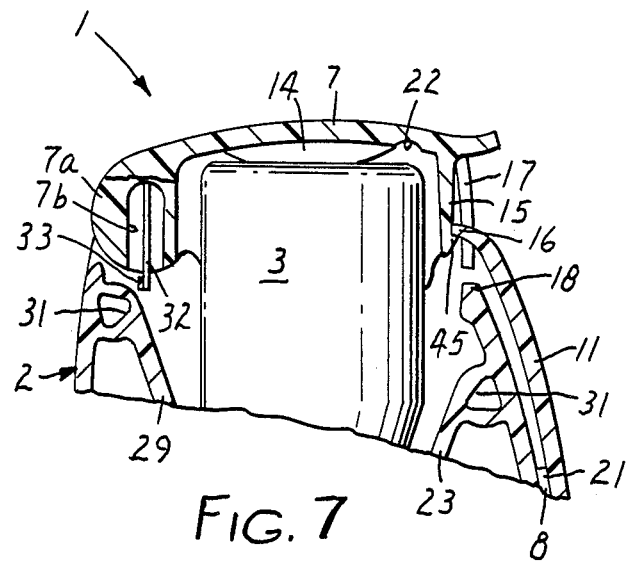
FIG. 7 is a cross sectional view of an embodiment of the dispenser, wherein the dispenserr comprises a spring means to hold the actuator such that the stop is removed from the catch. Upon opening, the gate will not contact the stop.
Figure 8:
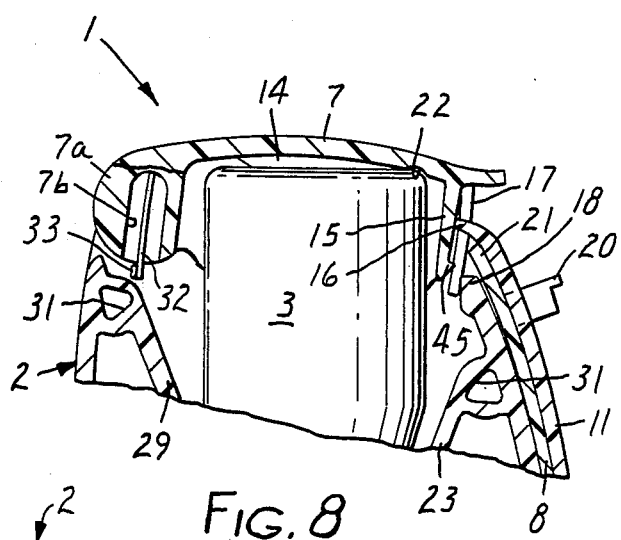
FIG. 8 is a further cross sectional view of the embodiment of the dispenser shown in FIG. 7 in the actuation mode, wherein the stop has been deflected past the catch.
Figure 9:
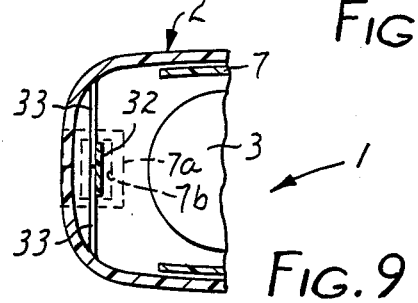
FIG. 9 is a partial cross sectional view of the embodiment of the dispenser shown in FIG. 7, which view further depicts the spring means.

The embodiment depicted in FIGS. 1–6 also features ridges 25 and 27 on gate 8, best seen in FIG. 3. With gate 8 in the closed position, ridge 27 is engaged with groove 26 in the inside surface of front section 11. Thus, when gate 8 is closed it is held closed with sufficient tenacity to prevent accidental opening. However, the user can easily open gate 8 for the purpose of using dispenser 1 by applying sufficient force to displace ridge 27 from groove 26. Upon complete retraction of gate 8 to the open position, ridge 25 engages groove 26. Thus, when gate 8 is in the open position it is held there with sufficient tenacity to prevent accidental closure. However, the user can easily close gate 8 for the purpose of storing the dispenser 1 in a fashion such that accidental actuation of the aerosol container assembly 3 is not possible.

FIGS. 7, 8, and 9 depict a further preferred embodiment of dispenser 1. In FIG. 7, actuator 7 has a spring tab 32 extending down from the top of chamber 7*b* and adapted to engage a complimentary spring tab 33 on the housing when the actuator is in the closed position. Spring 33 comprises two opposed tabs projecting from opposite sides of the housing. Spring tabs 32 and 33 may be integral with the actuator and the housing respectively. Engagement of the spring tabs 32 and 33 serves to hold the actuator in a position such that the hook 45 of latch 15 is engaged with flange 16. The actuator is so held with a force easily overcome by the user. Stop 17 is removed from catch 18, but upon attempted depression of the actuator with the gate in the closed position, stop 17 and catch 18 will engage and actuation will be prevented. When gate 8 is moved to its open position in this embodiment, as shown in FIG. 8, deflector 21 does not displace stop 17. Rather, deflector 21 is positioned such that stop 17 will be smoothly deflected away from catch 18 upon depression of the actuator.

The operation of the dispenser will be well understood through further discussion of the Figures.

FIG. 4 shows the dispenser 1 in its inactive mode. Aerosol container assembly 3 is held in place by the nozzle block 10 and by aerosol container assembly support structures 23 and 29. Actuator 7 is held in its closed position, with hook 45 of latch 15 engaged with hook 16. Therefore, aerosol container assembly 3 will not be accidentally displaced from its position inside the dispenser. Gate 8 is closed and held in the closed position by the engagement of groove 26 with ridge 27 (groove 26 and ridge 27 are best seen in FIG. 3). Open communication between valve stem 5 and mouthpiece 6 is thus interrupted. Furthermore, with gate 8 in its closed position, stop 17 is engaged with catch 18. Manual depression of actuator 7 to the actuating position is therefore prevented, and accidental actuation of the aerosol container assembly 3 can not occur.

FIG. 5 shows dispenser 1 in its ready mode. Gate 8 is in its open position and open communication exists between valve stem 5 and mouthpiece 6. Ridge 25 is engaged with groove 26 thus holding gate 8 in its open position. Furthermore, deflector means 21 has disengaged stop 17 from catch 18. Manual depression of actuator 7 and subsequent discharge of the aerosol formulation are possible.

FIG. 6 shows dispenser 1 in its actuation mode. Actuator 7 has been manually depressed to the actuating position. It is seen that relief 22 prevents contact between the actuator and the edge of the assembly 3, and the valve stem 5 is depressed to the point of actuation. A metered dose of aerosol is thus dispensed through the mouthpiece where it can be inhaled by the user.

While many materials are amenable to the construction of the dispenser of the present invention, it is preferred that the housing 2 is made of two halves of injection-molded high density polyethylene or Delrin® 500, a polyacetal homopolymer resin commercially available from E. I. duPont deNemours & Co., Inc., which pieces are joined together by mutually compatible male/female interlocking joints 31. These interlocking joints may be friction-fit joints or preferable snap-fit joints. The pieces are further held together by locking ring 28 which is snap-fit over the edge of mouth piece 6. The actuator 7 is preferably injection-molded Delrin® 500. The gate 8 and locking ring 28 are preferably injection-molded high density polyethylene.

The invention claimed is:

1. A dispenser for use with an aerosol container, the aerosol container having a valve for dispensing aerosol, the valve having a hollow valve stem which is movable relative to the container between an extended closed position and a depressed open position for discharge of aerosol, the dispenser comprising:

a housing with a front face terminating in a mouthpiece, which front face has an inside surface and which housing is adapted to receive an aerosol container and comprises a support block with a socket adapted to receive the valve stem, which support block has an orifice allowing open communication between the valve and the mouthpiece;

an actuator manually depressable between a closed position and an actuating position, having a first end pivotally mounted to the housing, a second manually depressable end, and a releasably engageable stop means to prevent unintended depression of the manually depressable end to the actuating position; and a catch means for preventing unintended depression of the actuator, which means is engageable with the stop means of the actuator when the actuator is in the closed position; and a gate means to open and close the mouthpiece, which gate means is mounted on the front face of the housing and comprises a wall section and a lift means to slide the wall section between a closed position in which the stop means of the actuator is engageable with the catch means, and the open communication between the valve and the mouthpiece is interrupted, and an open position in which open communication exists between the valve and the mouthpiece, and the stop means of the actuator is not engageable with the catch means thus permitting manual depression of the actuator to the actuating position.

2. A dispenser according to claim 1, wherein the actuator may be pivoted to an open position in which the manually depressable end of the actuator is remote from the housing and whereby an aerosol container may be placed in or removed from the dispenser.

3. A dispenser according to claim 1, wherein the actuator comprises a boss means to facilitate actuation of the aerosol container upon the depression of the manually depressable end of the actuator.

4. A dispenser according to claim 2, wherein the actuator comprises a releasably engaged latch means to prevent accidental pivoting of the actuator to the open position, in which open position unintended displacement of an aerosol container from the dispenser may occur.

5. A dispenser according to claim 4, wherein the housing comprises a flange which releasably engages the latch means of the actuator.

6. A dispenser according to claim 1, wherein the stop means and catch means are engaged with one another when the actuator is in the closed position and wherein the gate means comprises a deflector means for contacting the stop means of the actuator and displacing the stop means from engagement with the catch means when the gate means is in the open position.

7. A dispenser according to claim 1, wherein the actuator comprises a spring means to hold the stop means removed from the catch means when the actuator is in the closed position and wherein depression of the actuator causes the stop means to engage the catch means except when the gate means is in the open position.

8. A dispenser according to claim 1, wherein the housing comprises a front aerosol container assembly support structure and a rear aerosol container assembly support structure, which support structures define a chamber into which an aerosol container assembly may be placed.

9. A dispenser according to claim 8, wherein the front aerosol container assembly support structure comprises a surface adjacent to the inside surface of the front face of the housing.

10. A dispenser according to claim 8, wherein the gate means is slideable between the inside surface of the front face of the housing and the adjacent surface of the front aerosol container assembly support structure.

11. A dispenser according to claim 9, wherein the gate means includes a ridge and the inside surface of the front face of the housing contains a groove, which ridge engages the groove when the gate means is in the open position, thereby preventing the gate means when in the open position from falling back to the closed position.

12. A dispenser according to claim 1, wherein the lift means of the gate means is a tab which protrudes through a slot in the front face of the housing.

13. A dispenser according to claim 9, wherein the gate means includes a ridge and the inside surface of the front face of the housing includes a groove, which ridge engages the groove when the gate means is in the closed position, thereby preventing inadvertent movement of the gate means from the closed position.

14. A dispenser according to claim 1, wherein the housing comprises two halves joined by male/female interlocking joints.

15. A dispenser according to claim 1, wherein the housing is constructed of high density polyethylene.

16. A dispenser according to claim 1, wherein the actuator is constructed of a polyacetal homopolymer resin.

17. A dispenser according to claim 1, wherein the gate means is constructed of high density polyethylene.

18. A dispenser for use with an aerosol container, the aerosol container having a valve for dispensing aerosol, the valve having a hollow valve stem which is movable relative to the container between an extended closed position and a depressed open position for discharge of aerosol, the dispenser comprising:

a housing with a front face terminating in a mouthpiece, which front face has an inside surface and which housing is adapted to receive an aerosol container and comprises a support block with a socket adapted to receive the valve stem, which support block has an orifice allowing open communication between the valve and the mouthpiece;

an actuator manually depressable between a closed position and an actuating position, having a first end pivotally mounted to the housing, a second manually depressable end, and a releasably engageable stop means to prevent unintended depression of the manually depressable end to the actuating position; and a catch means for preventing unintended depression of the actuator, which means is engageable with the stop means of the actuator when the actuator is in the closed position; and a gate means to open and close the mouthpiece, which gate means is mounted on the front face of the housing and comprises a wall section and a lift means to slide the wall section between a closed position in which the stop means of the actuator is engageable with the catch means, and the open communication between the valve and the mouthpiece is interrupted, and an open position in which open communication exists between the valve and the mouthpiece, and the stop means of the actuator is not engageable with the catch means thus permitting manual depression of the actuator to the actuating position;

which housing further comprises a flange which releasably engages the latch means of the actuator; a front aerosol container assembly support structure and a rear aerosol container assembly support structure, which support structures define a chamber into which an aerosol container assembly may be placed; and which front aerosol container assembly support structure comprises a surface adjacent to the inside surface of the front face of the housing;

which actuator may be pivoted to an open position in which the manually depressable end of the actuator is remote from the housing and whereby an aerosol container may be placed in or removed from the dispenser, and which actuator further comprises: a boss means to facilitate actuation of the aerosol container upon the depression of the manually depressable end of the actuator; and a releasably engaged latch means to prevent accidental pivoting of the actuator to the open position, in which open position unintended displacement of an aerosol container from the dispenser may occur; and which gate means is slideable between the inside surface of the front face of the housing and the adjacent surface of the front aerosol container assembly support structure and further comprises a deflector section which contacts the stop means of the actuator and displaces the stop means from engagement with the catch means when the gate means is in the open position, thus permitting manual depression of the actuator to the actuating position.

* * * * *